(12) United States Patent
Simmons et al.

(10) Patent No.: US 10,744,240 B2
(45) Date of Patent: *Aug. 18, 2020

(54) ABDOMINAL TREATMENT SYSTEMS, DELIVERY DEVICES, AND METHODS

(71) Applicant: KCI Licensing, Inc., San Antonio, TX (US)

(72) Inventors: Tyler H. Simmons, San Antonio, TX (US); Alexander G. Sammons, San Antonio, TX (US)

(73) Assignee: KCI Licensinc, Inc., San Antonio, TX (US)

( * ) Notice: Subject to any disclaimer, the term of this patent is extended or adjusted under 35 U.S.C. 154(b) by 1007 days.

This patent is subject to a terminal disclaimer.

(21) Appl. No.: 14/989,533

(22) Filed: Jan. 6, 2016

(65) Prior Publication Data

US 2016/0193394 A1 Jul. 7, 2016

Related U.S. Application Data

(62) Division of application No. 13/903,818, filed on May 28, 2013, now Pat. No. 9,259,356, which is a division
(Continued)

(51) Int. Cl.
*A61M 1/00* (2006.01)
*A61F 13/00* (2006.01)

(52) U.S. Cl.
CPC ..... *A61M 1/0088* (2013.01); *A61F 13/00068* (2013.01)

(58) Field of Classification Search
CPC ........... A61M 1/0088; A61M 13/00068; A61F 13/00068
(Continued)

(56) References Cited

U.S. PATENT DOCUMENTS 1,355,846 A 10/1920 Rannells
2,547,758 A 4/1951 Kelling
(Continued)

FOREIGN PATENT DOCUMENTS

AU 550575 B2 3/1986
AU 745271 B2 3/2002
(Continued)

OTHER PUBLICATIONS

JP2015-227047—Japanese Notice of Rejection dated Jun. 27, 2017.
(Continued)

*Primary Examiner* — Andrew J Mensh

(57) ABSTRACT

A reduced-pressure abdominal treatment device is presented that has a plurality of liquid-impermeable layers with a foam spacer between two of the liquid-impermeable layers. The plurality of liquid-impermeable layers have a coextensive area $A_1$. The foam spacer has a plan-view area $A_2$. $A_2$ is less than 80% of $A_1$ (i.e., $A_2 < 0.8\ A_1$). The foam spacer is configured such that, under reduced pressure, a target fluid removal zone experiences reduced-pressure vectors over an angle theta ($\theta$) that is typically 360 degrees for a majority of locations in the target fluid removal zone. Applying 360 degrees of reduced pressure helps avoid blockage. The plurality of liquid-impermeable layers may be bonded for various effects. Other devices, systems, and methods are disclosed.

11 Claims, 8 Drawing Sheets

Related U.S. Application Data of application No. 13/043,987, filed on Mar. 9, 2011, now Pat. No. 8,469,935.

(60) Provisional application No. 61/312,990, filed on Mar. 11, 2010.

(58) Field of Classification Search
USPC .......................................................... 604/319
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,544 A * | 9/1990 | Hansen ................... A61F 7/10 428/903 |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,794,438 B2 * | 9/2010 | Henley ............... A61M 1/0088 604/289 |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0030304 A1 * | 2/2004 | Hunt ................... A61M 1/0088 604/317 |
| 2008/0294127 A1 | 11/2008 | Blott et al. |
| 2009/0204084 A1 | 8/2009 | Blott et al. |
| 2011/0152796 A1 * | 6/2011 | Kazala, Jr. .......... A61M 1/0088 604/290 |
| 2012/0041402 A1 * | 2/2012 | Greener ............ A61F 13/00068 604/319 |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| CA | 2741745 | 6/2010 |
| CN | 1438904 A | 8/2003 |
| DE | 26 40 413 A1 | 3/1978 |

(56) References Cited

FOREIGN PATENT DOCUMENTS

| | | |
|---|---|---|
| DE | 43 06 478 A1 | 9/1994 |
| DE | 29 504 378 U1 | 9/1995 |
| EP | 0100148 A1 | 2/1984 |
| EP | 0117632 A2 | 2/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 2003-532504 A | 11/2003 |
| JP | 4129536 B2 | 8/2008 |
| JP | 2009508549 A | 3/2009 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 01/85248 A1 | 11/2001 |
| WO | 2007031757 A1 | 3/2007 |
| WO | 2008039839 A2 | 4/2008 |
| WO | 09066105 A1 | 5/2009 |
| WO | 2009111657 A2 | 9/2009 |

OTHER PUBLICATIONS

EP Search Report for EP11710939.7 dated Jan. 19, 2015.
Louis C. Argenta, MD and Michael J. Morykwas, PHD; Vacuum-Assisted Closure: A New Method for Wound Control and Treatment: Clinical Experience; Annals of Plastic Surgery.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract,

(56) References Cited

OTHER PUBLICATIONS editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
European Search Report dated Jun. 3, 2016, corresponding to EP Application No. 16157204.
Japanese Notice of Rejection corresponding to JP2015-227047, dated Nov. 1, 2016.
Canadian Examination Report corresponding to CA2,789,002, dated Mar. 3, 2017.
Japanese Notice of Rejection for Corresponding Application No. 2018-024620, dated Dec. 18, 2018.

\* cited by examiner

ABDOMINAL TREATMENT SYSTEMS, DELIVERY DEVICES, AND METHODS

RELATED APPLICATION

This application is a Divisional of U.S. patent application Ser. No. 13/903,818, filed May 28, 2013, which is a Divisional of U.S. patent application Ser. No. 13/043,987 filed Mar. 9, 2011, now U.S. Pat. No. 8,469,935, which claims the benefit, under 35 USC § 119(e), of the filing of U.S. Provisional Patent Application Ser. No. 61/312,990, entitled "Abdominal Treatment Systems, Delivery Devices, and Methods," filed Mar. 11, 2010, which is incorporated herein by reference for all purposes.

BACKGROUND

The present disclosure relates generally to medical treatment systems, and more particularly, to abdominal treatment systems, delivery devices, and methods for treating an abdominal cavity using reduced pressure.

Depending on the medical circumstances, reduced pressure may be used for, among other things, reduced-pressure therapy to encourage granulation at a tissue site or for draining fluids at a tissue site. As used herein, unless otherwise indicated, "or" does not require mutual exclusivity. Both reduced-pressure therapy and drainage with reduced pressure often involve manifolding, or distributing, reduced pressure to the tissue site.

SUMMARY

According to an illustrative, non-limiting embodiment, an abdominal treatment delivery device for distributing reduced pressure to a tissue site in an abdominal cavity and removing fluids includes a plurality of liquid-impermeable layers that are proximate to one another and a foam spacer disposed between at least two layers of the plurality of liquid-impermeable layers. The plurality of liquid-impermeable layers has a coextensive area $A_1$ and the liquid-impermeable layers are fenestrated. The foam spacer has a plan-view area $A_2$, and $A_2$ is less than 80% of $A_1$ (i.e., $A_2 < 0.8 A_1$). The foam spacer is configured and located such that, under reduced pressure, a target fluid removal zone experiences reduced-pressure vectors over an angle theta ($\theta$) that is 360 degrees for a majority of locations in the target fluid removal zone.

According to another illustrative, non-limiting embodiment, a system for treating an abdominal cavity with reduced pressure includes an abdominal treatment device for distributing reduced pressure to a tissue site and a reduced-pressure source. The reduced-pressure source is fluidly coupled to the abdominal treatment device. The abdominal treatment device includes a plurality of liquid-impermeable layers that are proximate to one another and a foam spacer disposed between at least two layers of the plurality of liquid-impermeable layers. The plurality of liquid-impermeable layers has a coextensive area $A_1$ and is fenestrated. The foam spacer has a plan-view area $A_2$, and $A_2$ is less than 80% of $A_1$ (i.e., $A_2 < 0.8 A_1$). The foam spacer is configured such that, under reduced pressure, a target fluid removal zone experiences reduced-pressure vectors over an angle theta ($\theta$) that is 360 degrees for a majority of locations in the target fluid removal zone.

According to another illustrative, non-limiting embodiment, a method of manufacturing an abdominal treatment device includes the steps of: providing a plurality of liquid-impermeable layers that are fenestrated and disposing a foam spacer between at least two layers of the plurality of liquid-impermeable layers. The plurality of liquid-impermeable layers has a coextensive area $A_1$. The foam spacer disposed between at least two layers of the plurality of liquid-impermeable layers has a plan-view area $A_2$, and $A_2$ is less than 80% of $A_1$ (i.e., $A_2 < 0.8 A_1$). The foam spacer is configured and located such that, under reduced pressure, a target fluid removal zone experiences reduced-pressure vectors over an angle theta ($\theta$) that is 360 degrees for a majority of locations in the target fluid removal zone.

According to another illustrative, non-limiting embodiment, a method of treating a tissue site in an abdominal cavity includes the steps of: opening the abdominal cavity to form an open cavity; deploying within the abdominal cavity an abdominal treatment delivery device; deploying a reduced-pressure connector subsystem; and deploying a sealing member to form a fluid seal over the open cavity. The method further includes fluidly coupling the reduced-pressure connector subsystem to a reduced-pressure source and activating the reduced-pressure source. The abdominal treatment device includes a plurality of liquid-impermeable layers that are proximate to one another and a foam spacer disposed between at least two layers of the plurality of liquid-impermeable layers. The plurality of liquid-impermeable layers has a coextensive area $A_1$ and is fenestrated. The foam spacer has a plan-view area $A_2$, and $A_2$ is less than 80% of $A_1$ (i.e., $A_2 < 0.8 A_1$). The foam spacer is configured and located such that, under reduced pressure, a target fluid removal zone experiences reduced-pressure vectors over an angle theta ($\theta$) that is 360 degrees for a majority of locations in the target fluid removal zone.

Other features and advantages of the illustrative embodiments will become apparent with reference to the drawings and detailed description that follow.

DETAILED DESCRIPTION

In the following detailed description of the non-limiting, illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
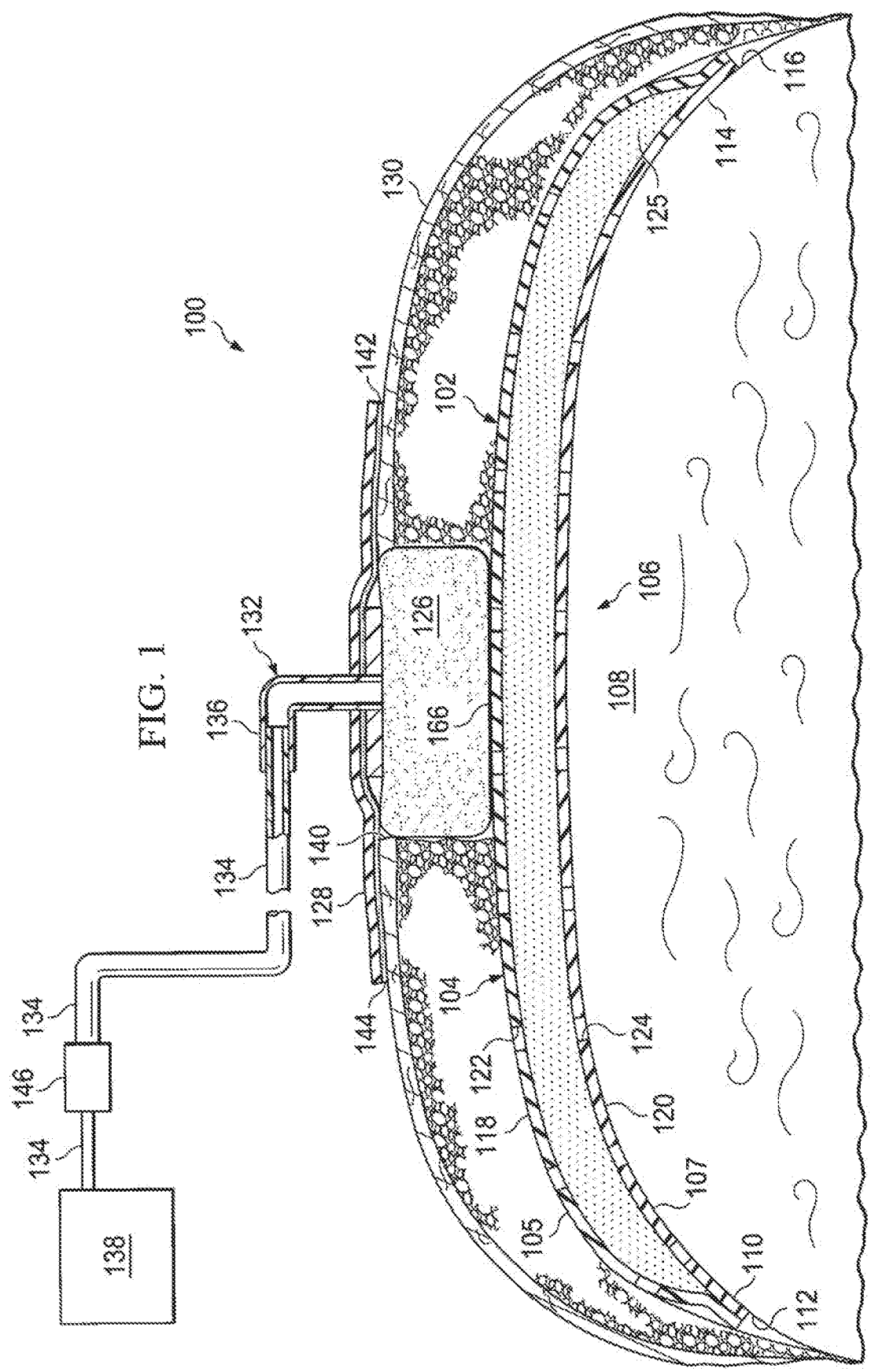
FIG. 1 is a schematic diagram with a portion in cross section of an illustrative system for treating an abdominal cavity.
Figure 2:
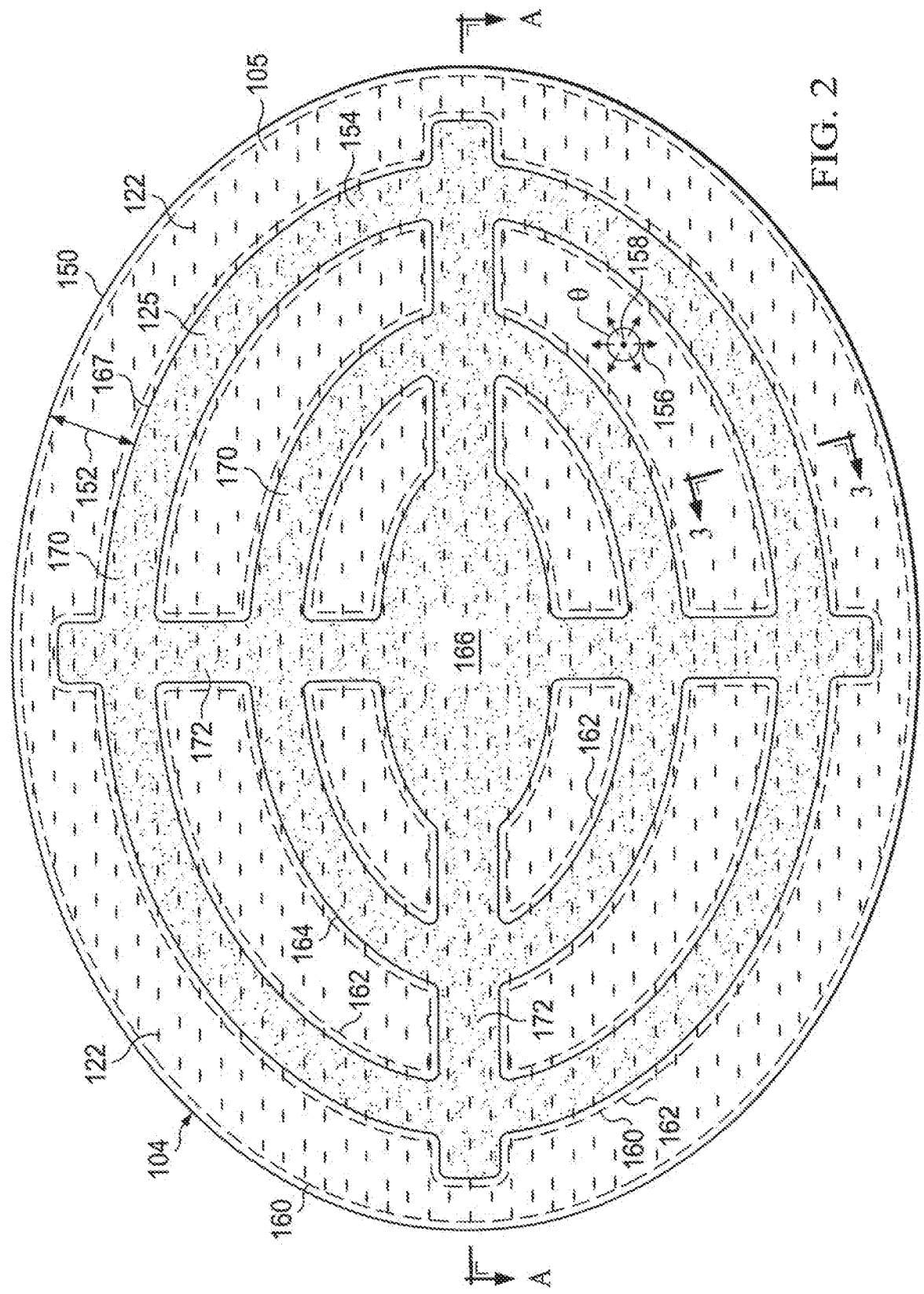
FIG. 2 is a schematic, plan view of an illustrative abdominal treatment device.

Referring now to FIGS. 1 and 2, an illustrative embodiment of a system 100 for treating an abdominal cavity 102 is presented. The system 100 includes an abdominal treatment device 104. The system 100 and the abdominal treatment device 104 are for treating a tissue site 106 of a patient. The tissue site 106 may be the bodily tissue of any human, animal, or other organism. In this illustrative embodiment, the tissue site 106 includes tissue in a body cavity, and in particular the abdominal cavity 102. The tissue site 106 includes the abdominal contents 108 or tissue that is proximate the abdominal cavity 102. Treatment of the tissue site 106 may include removal of fluids, e.g., ascites, protection of the abdominal cavity, or reduced-pressure therapy.

As shown in FIG. 1, the abdominal treatment device 104 is disposed within the abdominal cavity 102 of the patient to treat the tissue site 106. The abdominal treatment device 104 is supported by the abdominal contents 108. The abdominal contents 108 include a surface on which the abdominal treatment device 104 is positioned. A portion 110 of the abdominal treatment device 104 may be positioned in or proximate to a first paracolic gutter 112, and another portion 114 may be placed in or proximate to a second paracolic gutter 116.

The abdominal treatment device 104 is formed with a plurality of liquid-impermeable layers 117, e.g., a first liquid-impermeable layer 118 and a second liquid-impermeable layer 120. FIG. 1 is a schematic drawing and is not to scale. The plurality of liquid-impermeable layers 117, e.g., layers 118, 120, is formed with fenestrations 122, 124, respectively. "Liquid impermeable" with respect to "liquid-impermeable layers" means that the layers are formed with a liquid-impermeable material. Thus, although formed with a liquid-impermeable material, the layer may be liquid permeable when fenestrated, but nonetheless is referred to as a liquid-impermeable layer. The fenestrations 122, 124 may take any shape, e.g., circular apertures, rectangular openings, polygons, or any other shape. The fenestrations 122, 124 are presented in this illustrative embodiment as slits, or linear cuts. As described more fully below, a foam spacer 125 is disposed between at least two layers of the plurality of liquid-impermeable layers, e.g., the first liquid-impermeable layer 118 and the second liquid-impermeable layer 120. In considering FIG. 1, note that the portion of the abdominal treatment device 104 shown is based on a cross section taken along line A-A in FIG. 2. The abdominal treatment device 104 has a first side 105 and a second, tissue-facing side 107. The abdominal treatment device 104 is typically symmetrical such that the sides 105, 107 are same. Reference to different sides of the abdominal treatment device 104 is made for explanation purposes.

A manifold 126, or manifold pad, distributes reduced pressure to the abdominal treatment device 104. A sealing member 128 provides a fluid seal over the abdominal cavity 102. One or more skin closure devices may be placed on a patient's epidermis 130.

A reduced-pressure connector subsystem 132 may be used to fluidly connect the abdominal treatment device 104 to a reduced-pressure conduit 134. The reduced-pressure connector subsystem 132 may include a reduced-pressure connector 136, or interface, and the manifold 126. Alternatively, the reduced-pressure connector subsystem 132 may be an in situ connector (not shown) on the abdominal treatment device 104 or any other device for supplying reduced pressure to the abdominal treatment device 104. The reduced-pressure conduit 134 is fluidly coupled to a reduced-pressure source 138.

Thus, in one illustrative embodiment, reduced pressure is delivered to the abdominal treatment device 104 through the manifold 126 which receives reduced pressure through the reduced-pressure connector 136, which is coupled to the reduced-pressure delivery conduit 134. The reduced-pressure source 138 delivers reduced pressure to the reduced-pressure delivery conduit 134.

The reduced pressure may be applied to the tissue site 106 to help promote removal of ascites, exudates, or other fluids from the tissue site 106. In some instances, reduced pressure may be applied to stimulate the growth of additional tissue. In some instances, only fluid removal may be desired. As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Reduced pressure may initially generate fluid flow in the manifold 126, the reduced-pressure delivery conduit 134, and proximate the tissue site 106. As the hydrostatic pressure around the tissue site 106 approaches the desired reduced pressure, the flow may subside, and the reduced pressure may be maintained. Unless otherwise indicated, values of pressure stated herein are gauge pressures. Although the terms "vacuum" and "negative pressure" may be used to describe the pressure applied to the tissue site, the actual pressure applied to the tissue site may be more than the pressure normally associated with a complete vacuum. Consistent with the use herein, unless otherwise indicated, an increase in reduced pressure or vacuum pressure typically refers to a relative reduction in absolute pressure.

The manifold 126 is shown adjacent to the abdominal treatment device 104. The manifold 126 may take many forms. The term "manifold" as used herein generally refers to a substance or structure that is provided to assist in applying reduced pressure to, delivering fluids to, or removing fluids from the tissue site 106 or other location. The manifold 126 typically includes a plurality of flow channels or pathways that distribute the fluids provided to and removed around the manifold 126. In one illustrative embodiment, the flow channels or pathways are interconnected to improve distribution of fluids provided or removed from the tissue site 106. The manifold 126 may be a biocompatible material that is capable of being placed in contact with tissue site. Examples of the manifold 126 may include, without limitation, devices that have structural elements arranged to form flow channels, cellular foam, such as open-cell foam, porous tissue collections, liquids, gels and foams that include or cure to include flow channels. The manifold 126 may be porous and may be made from foam, gauze, felted mat, or any other material suited to a particular biological application.

In one embodiment, the manifold 126 is a porous foam and includes a plurality of interconnected cells or pores that act as flow channels. The porous foam may be a polyurethane, open-cell, reticulated foam, such as a GranuFoam® material manufactured by Kinetic Concepts, Incorporated of San Antonio, Tex. Other embodiments might include "closed cells." In some situations, the manifold 126 may also be used to distribute fluids, such as medications, antibacterials, growth factors, and various solutions to the tissue site 106 or to another location. Other layers may be included in or on the manifold 126, such as absorptive materials, wicking materials, hydrophobic materials, and hydrophilic materials. The foam spacer 125 in the abdominal treatment device 104 may be made from any of the same materials as the manifold 126. For example, and not by way of limitation, the foam spacer 125 may be a polyurethane, open-cell, reticulated foam, such as a GranuFoam® material.

The sealing member 128 is placed over the abdominal cavity 102 and provides a fluid seal. As used herein, "fluid seal," or "seal," means a seal adequate to maintain reduced pressure at a desired site given the particular reduced-pressure source 138 or subsystem involved. The sealing member 128 may be a cover that is used to secure the manifold 126 on a portion of the abdominal treatment device 104. The sealing member 128 may be impermeable or semi-permeable. The sealing member 128 is capable of maintaining reduced pressure at the tissue site 106 after installation of the sealing member 128 over the abdominal cavity 102 and particularly an abdominal cavity opening 140. The sealing member 128 may be a flexible over-drape or film formed from a silicone-based compound, acrylic, hydrogel or hydrogel-forming material, or any other biocompatible material that includes the impermeability or permeability characteristics as desired for applying reduced pressure to the tissue site 106.

The sealing member 128 may further include an attachment device 142 to secure the sealing member 128 to the patient's epidermis 130. The attachment device 142 may take many forms. For example, the attachment device may be an adhesive layer 144 that may be positioned along a perimeter, the entirety of, or any portion of the sealing member 128 to provide, directly or indirectly, the fluid seal with the patient's epidermis 130. The adhesive layer 144 may also be pre-applied to the sealing member 128 and covered with a releasable backing, or member (not shown), that is removed at the time of application.

The reduced-pressure connector 136 may be, as one example, a port or connector, which permits the passage of fluid from the manifold 126 to the reduced-pressure delivery conduit 134 and vice versa. For example, fluid collected from the tissue site 106 using the manifold 126 and the abdominal treatment device 104 may enter the reduced-pressure delivery conduit 134 via the reduced-pressure connector 136. In another embodiment, the system 100 may omit the reduced-pressure connector 136 and the reduced-pressure delivery conduit 134 may be inserted directly into the sealing member 128 and into the manifold 126. The reduced-pressure delivery conduit 134 may be a medical conduit or tubing or any other device for transporting a reduced pressure and fluid. The reduced-pressure delivery conduit 134 may be a multi-lumen member. In one embodiment, the reduced-pressure delivery conduit 134 is a two-lumen conduit with one lumen for reduced pressure and liquid transport and one lumen for communicating pressure to a pressure sensor.

Reduced pressure is supplied to the reduced-pressure delivery conduit 134 by the reduced-pressure source 138. A wide range of reduced pressures may be supplied by the reduced-pressure source 138. In one embodiment, the pressure may be in the range −50 to −300 mm Hg and in another embodiment, in the range of −100 mm Hg to −200 mm Hg. The pressure may be, for example, −100, −110, −120, −125, −130, −140, −150, −160, −170, −180, −190, or −200 mm Hg. In one illustrative embodiment, the reduced-pressure source 138 includes preset selectors for −100 mm Hg, −125 mm Hg, and −150 mm Hg. The reduced-pressure source 138 may also include a number of alarms, such as a blockage alarm, a leakage alarm, or a battery-low alarm. The reduced-pressure source 138 could be a portable source, wall source, or other unit for abdominal cavities. The reduced-pressure source 138 may selectively deliver a constant pressure, varied pressure (patterned or random), intermittent pressure, or continuous pressure. The fluid removed from the cavity through the reduced-pressure delivery conduit 134 could be as much as 5L or more per day depending on the circumstances. A canister or fluid reservoir for receiving removed fluids may be associated with the reduced-pressure source 138.

A number of different devices, e.g., device 146, may be added to a portion of the reduced-pressure delivery conduit 134. For example, the device 146 may be a fluid reservoir, or canister collection member, a pressure-feedback device, a volume detection system, a blood detection system, an infection detection system, a filter, a flow monitoring system, a temperature monitoring system, or other device. Multiple devices 146 may be included. Some of these devices, e.g., the fluid collection member, may be formed integrally with the reduced-pressure source 138.

Figure 3:
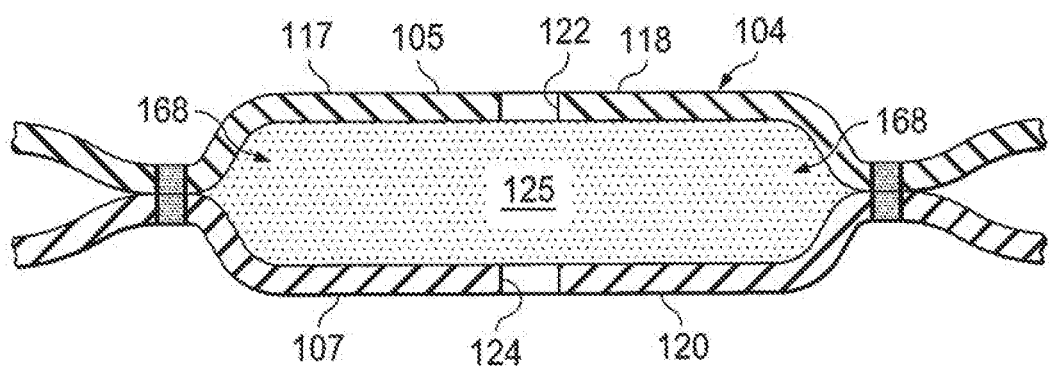
FIG. 3 is a schematic, cross-sectional view of a portion of the illustrative abdominal treatment device of FIG. 2 taken along line 3-3.

Referring now primarily to FIGS. 2 and 3, the abdominal treatment device 104 is flexible and easily positioned within the abdominal cavity. At the same time, the abdominal treatment device 104 is adapted to avoid blockage at discrete locations on the abdominal treatment device 104 by having fluid flow over a large range of directions. In order to facilitate flexibility, the abdominal treatment device 104 may be formed with the foam spacer 125 smaller than the liquid-impermeable layers 117.

The abdominal treatment device 104 includes the plurality of liquid-impermeable layers 117, e.g., the first liquid-impermeable layer 118 and the second liquid-impermeable layer 120. The micro-channel 168 space is formed between adjacent layers of the plurality of liquid-impermeable layers 117. Additional layers may be included in the plurality of liquid-impermeable layers 117. The plurality of liquid-impermeable layers 117 is formed with fenestrations, e.g., fenestrations 122, 124, and the layers of the plurality of liquid-impermeable layers 117 are placed proximate to one another to form a substantially flat member having a co-extensive area $A_1$.

The coextensive area $A_1$ is the plan view area (before insertion) of where the layers of the plurality of liquid-impermeable layers 117 that are adjacent to the foam spacer 125 are co-extensive with one another. The foam spacer 125 is disposed between at least two layers of the plurality of liquid-impermeable layers 117. The plurality of liquid-impermeable layers 117 may be formed from the same materials as the sealing member 128. In one embodiment, each of the liquid-impermeable layers 117 may be of a thickness in the range of 50 to 120 microns and in another non-limiting embodiment may be approximately 80 microns.

The foam spacer 125 has a plan-view area $A_2$, e.g., the area shown in plan view, that is less than the coextensive area $A_1$ of the plurality of liquid-impermeable layers 117. The plan-view area $A_2$ is less than the coextensive area $A_2$ of the plurality of liquid-impermeable layers 117 at least in part to enhance flexibility. Typically, the plan-view area $A_2$ is less than 80 percent (80%) of the coextensive area $A_1$ of the plurality of liquid-impermeable layers 117, i.e. $A_2<0.8 A_1$. The plan-view area $A_2$ may be less of a percentage of $A_1$, e.g., $A_2<0.7 A_1$, $A_2<0.6 A_1$, $A_2<0.5 A_1$, $A_2<0.4 A_1$, $A_2<0.3 A_1$, $A_2<0.2A_1$, $A_2<0.1 A_1$, etc.

Figure 5:
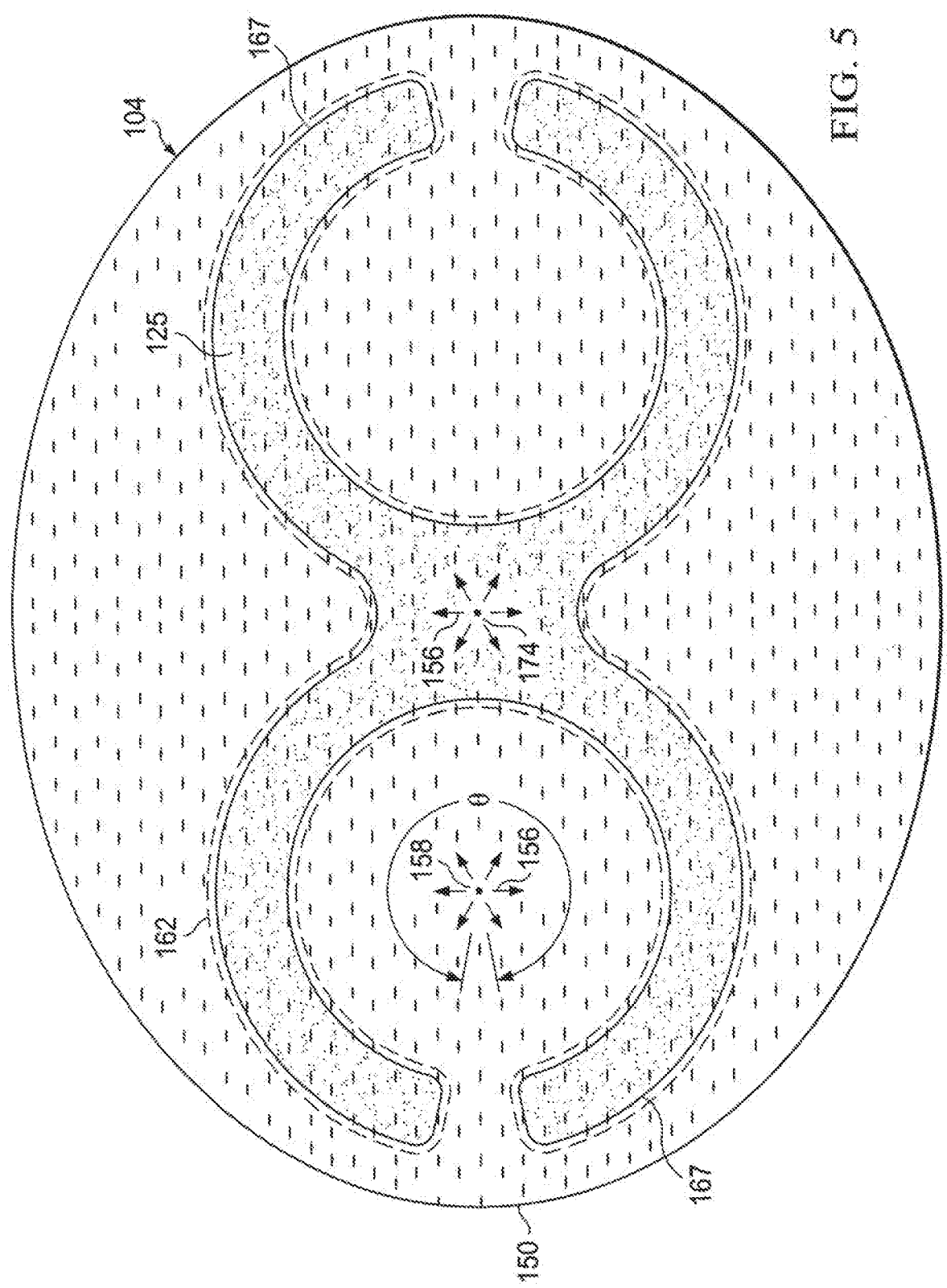
FIG. 5 is another schematic, plan view of another illustrative abdominal treatment device.

A plurality of bonds 160 may be used to couple at least two layers of the plurality of liquid-impermeable layers 117. Any pattern or random bonds may be used for the plurality of bonds 160. The bonds may be formed using any known technique, including without limitation, welding (e.g., ultrasonic or RF welding), bonding, adhesives, cements, or other bonding technique or apparatus. The plurality of bonds 160 may include spacer bonds 162 that may be around or surround edges 164 of the foam spacer 125 as shown in plan view. The spacer bonds 162 may be a stitch bond as shown in FIG. 2 or a solid bond as shown in FIG. 5. The spacer bonds 162 help secure the foam spacer 125 in a fixed position relative to the plurality of liquid-impermeable layers 117.

The fenestrations, e.g., fenestrations 122, 124, allow fluids to enter the space between the plurality of liquid-impermeable layers 117. The fluids that enter the fenestrations 122, 124 move directly or indirectly towards a reduced-pressure source. A reduced pressure may be, and typically is, applied to a center portion 166 of the abdominal treatment device 104 or elsewhere to cause fluid flow through the fenestrations 122, 124 and within the foam spacer 125 or micro-channels 168 (FIG. 3) formed between adjacent layers of the plurality of liquid-impermeable layers 117. Typically, the foam spacer 125 communicates reduced pressure within the plurality of liquid-impermeable layers 117 and often will be a dominant source of reduced-pressure. The reduced pressure at various locations may be represented by pressure vectors, e.g., reduced-pressure vectors 156 (FIG. 2).

While flexibility is desired for the abdominal treatment device 104, blockage avoidance is also desired. If an abdominal device 104 only had a center portion 166, a point in the micro-channel 168, or between liquid impermeable layers, would experience reduced pressure moving fluids in substantially one direction, or over a limited angle depending on its distance from the center portion 166. If that unidirectional path becomes blocked, the flow in a particular area may largely stop. The present embodiment of the abdominal treatment device 104 delivers reduced pressure over a large angle, e.g., 270-360 degrees, for a given point. Typically, reduced pressure is experienced in all directions (360 degrees). The foam spacer 125 provides the strongest source of reduced pressure within the micro-channels 168 and influences the flow directions.

Referring to FIGS. 2 and 3, consider a cylindrical analytical control volume 158, which is a control volume for analyzing pressure at a location in the micro-channel 168. The control volume 158 experiences reduced pressure over 360 degrees. The abdominal treatment device 104 may have all the analytical control volumes, e.g., analytical control volume 158, within a treatment area, or target fluid removal zone, experiencing 360 degrees of reduced pressure. Thus, if a blockage occurs in one direction for a analytical control volume, fluid may continue to move in other directions. The angle over which the reduced pressure acts on a given analytical control volume, e.g., analytical control volume 158, is defined as angle theta (θ).

The area of the abdominal treatment device 104 that experiences greater than 270 degrees of reduced pressure may be defined as a target fluid removal zone. For example, the area may experience 270, 280, 290, 300, 310, 320, 330, 340, 350, or 360 degrees of reduced pressure. The target fluid removal zone is generally defined as the area bound substantially by an outer peripheral edge of the foam spacer 125 making allowances for any discontinuities. Thus, for the abdominal treatment device of FIG. 2, the target fluid removal zone exists on the portion of the abdominal treatment device 104 that is inboard from a peripheral edge 150 by a distance 152. In other words, the target fluid removal zone is from a peripheral edge 167 of the foam spacer 125 (or from the outer edge of a concentric circle 154) and inward. In other illustrative embodiments, the target fluid removal zone may have portions in which the analytical control volumes would have an angle theta (θ) less than 360 degrees, e.g., 270 degrees, but preferably the majority, i.e., >50%, of locations analyzed will have 360 degrees of reduced pressure acting upon them. In other embodiments, the target flow zone may be defined as having more than 70 percent (70%) of the locations experiencing reduced pressure in 360 degrees. As shown in FIG. 2, the foam spacer 125 may be formed with a plurality of windows or window openings, such as where cylindrical analytical control volume 158 is shown.

Figure 4B:
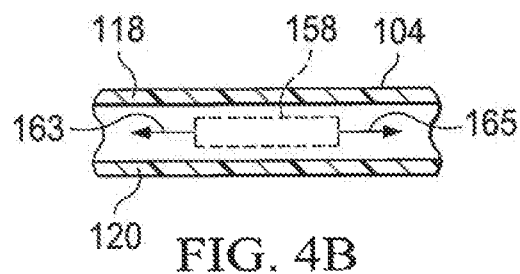
FIG. 4B is a schematic cross section of a portion of the abdominal treatment device of FIG. 4A taken along line 4B-4B.
Figure 4A:
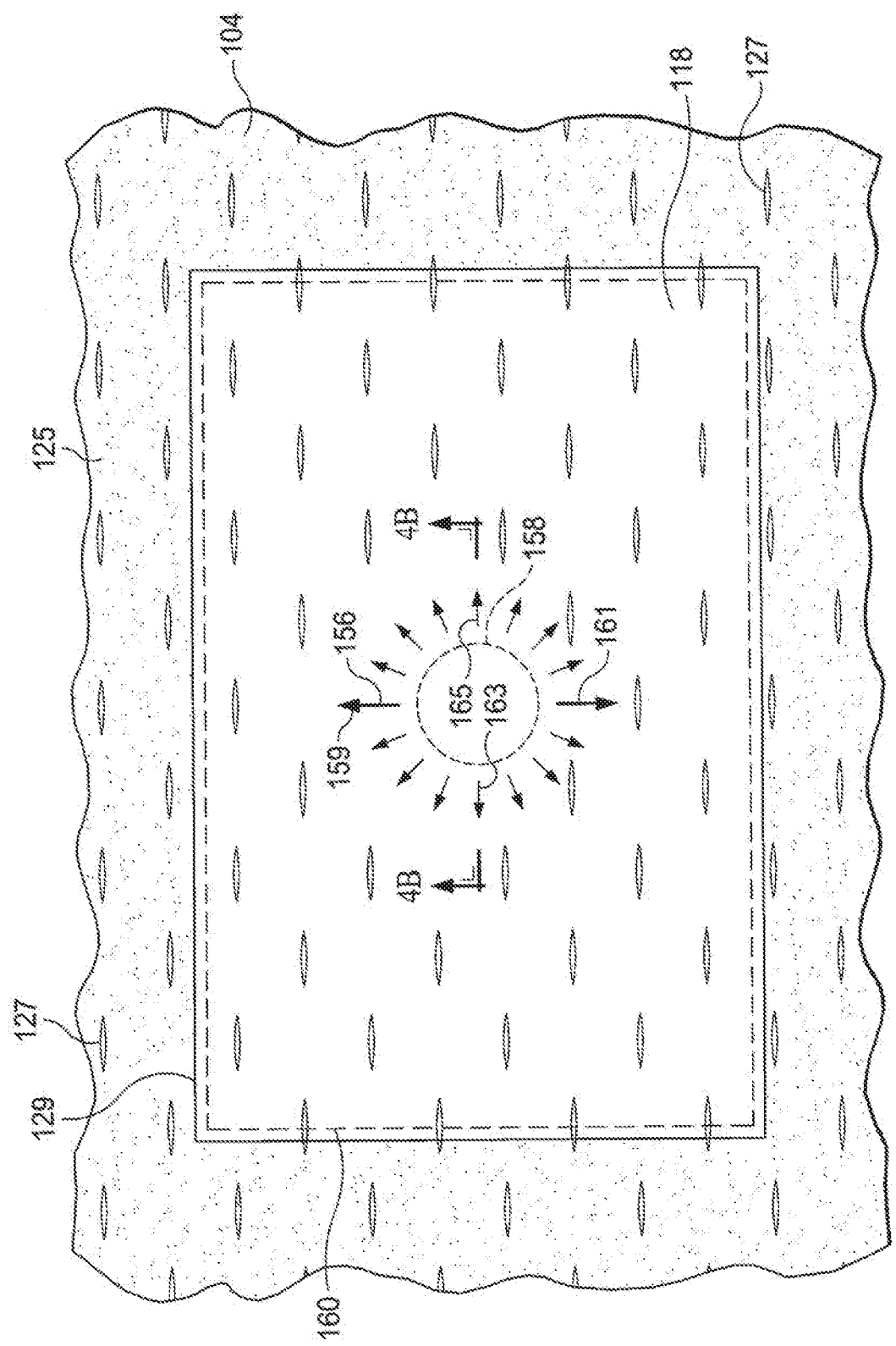
FIG. 4A is a schematic plan view of a portion of an abdominal treatment device.

Referring now to FIGS. 4A and 4B, a portion of an abdominal treatment device 104 is presented. The portion shows portions of a foam spacer 125 under a first liquid-impermeable layer 118 having fenestrations 127. The first liquid-impermeable layer 118 is bonded with bonds 160 to a second liquid-impermeable layer 120 with the foam spacer 125 therebetween. A window 129 is formed by the foam spacer 125 in this portion of target fluid removal zone. Because the foam spacer 125 of the window 129 provides the main delivery of reduced pressure, an analytical control volume 158 experiences reduced pressure vectors 158 over angle theta of 360 degrees.

Often, the reduced pressure in a given direction will be related to the distance from the analytical control volume 158 to the foam spacer 125 in a given direction. Thus, for FIG. 4A, a first reduced-pressure vector 159 and a second reduced-pressure vector 161 are the greatest because they are at locations closest to the foam spacer 125. Third and fourth reduced-pressure vectors 163 and 165 are the least because they are the farthest from the foam spacer 125 in a given direction.

The foam spacer 125 may take numerous possible shapes. The shape and size of the foam spacer 125 are typically selected to promote flexibility of the abdominal treatment device 104, i.e., to make the abdominal treatment device 104 compliant. The flexibility typically helps place the abdominal treatment device 104 or a portion of the abdominal treatment device 104 in difficult-to-reach locations, such as the paracolic gutters 112 and 116, and helps remove the abdominal treatment device 104 in certain situations. With respect to the latter, the abdominal treatment device 104 may be applied in some situations through an open abdomen with a directly connecting reduced-pressure delivery conduit 134, the abdominal cavity opening 140 closed, and then later the abdominal treatment device 104 may be removed through a surgical incision, e.g., an incision in the range of 5 centimeters to 40 centimeters—or any sub-range thereof.

In addition to flexibility, the shape of the foam spacer 125 may be selected to promote a range of reduced-pressure vectors 156 in a target flow zone or to direct flow. In the illustrative embodiment of FIG. 2, the foam spacer 125 is formed as a plurality of arced members, e.g., concentric circles or elliptical members, 170 that are interconnected by members 172. The target treatment zone may experience 360 degrees of reduced pressure. FIG. 5 presents another illustrative shape.

Referring now primarily to FIG. 5, the foam spacer 125 of the abdominal treatment device 104 includes mirrored c-shaped members that are interconnected. The foam spacer 125 is formed with spacer bonds 162 that are one or more solid bonds. In this embodiment, analytical control volumes, such as analytical control volume 158, in the target flow zone experience reduced-pressure vectors 156 that may be less than 360 degrees but greater than 270 degrees. Other points, e.g., interior point 174, may experience 360 degrees of reduced-pressure vectors 156. The target flow zone for this embodiment is inboard of the outer peripheral edge 167 of the foam spacer 125. A majority, e.g., >50%, of the locations of the target flow zone experience reduced pressure in 360 degrees and thereby help minimize the chance of blockage inhibiting flow. In other embodiments, the target flow zone may be defined as having more than 70 percent (70%) of the locations experiencing reduced pressure in 360 degrees.

Figure 6:
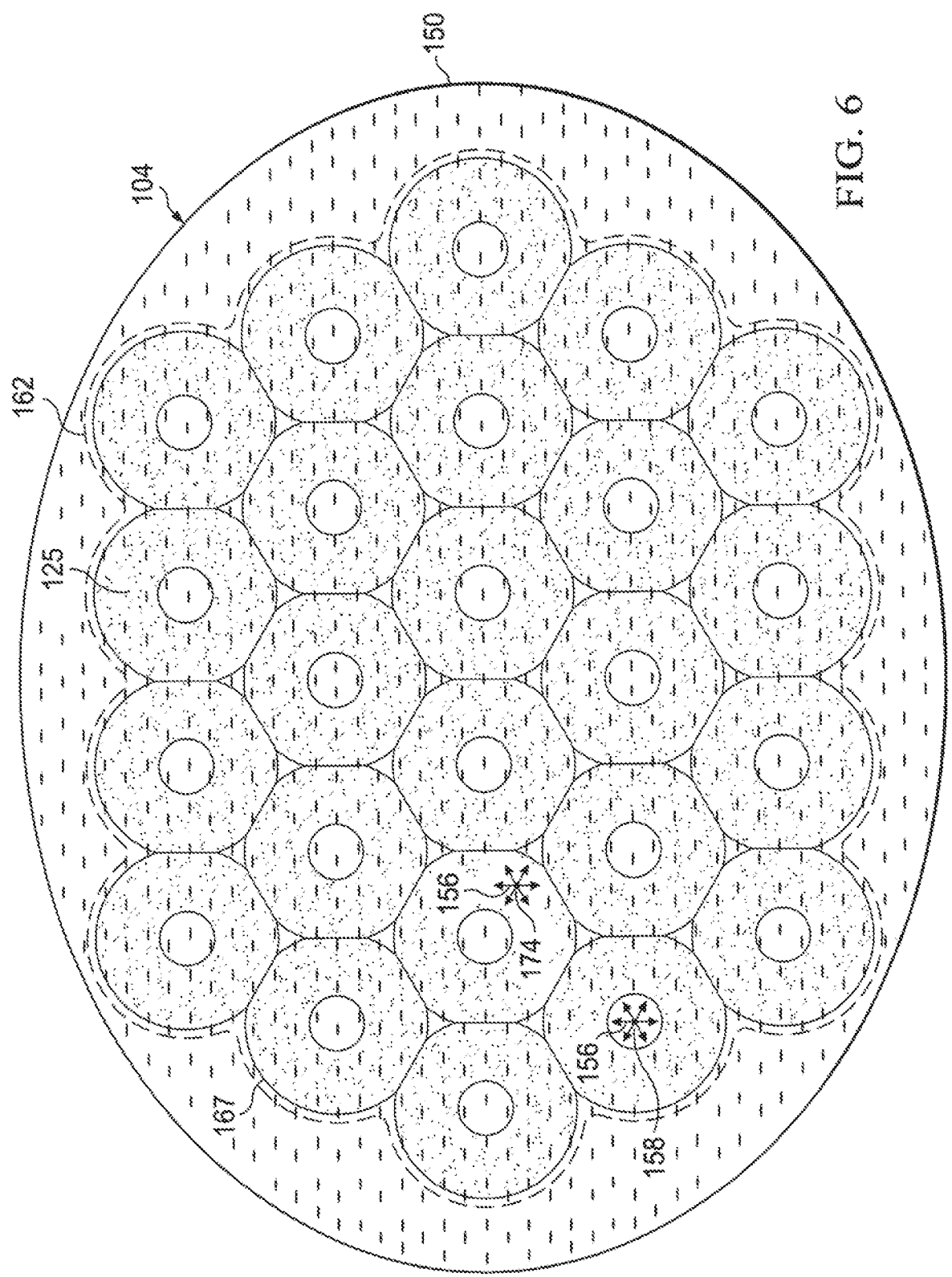
FIG. 6 is a schematic, plan view of another illustrative abdominal treatment device.

As another non-limiting example of a shape that the foam spacer 125 of the abdominal treatment device 104 may take, FIG. 6 presents a foam spacer 125 formed as a plurality of interconnected, annular circles. In this embodiment, analytical control volumes (e.g., first analytical control volume 158 and second analytical control volumes 174), experience 360 degrees of reduced-pressure vectors 156. The spacer bonds 162 are shown as a stitch bond in this example.

Figure 7:
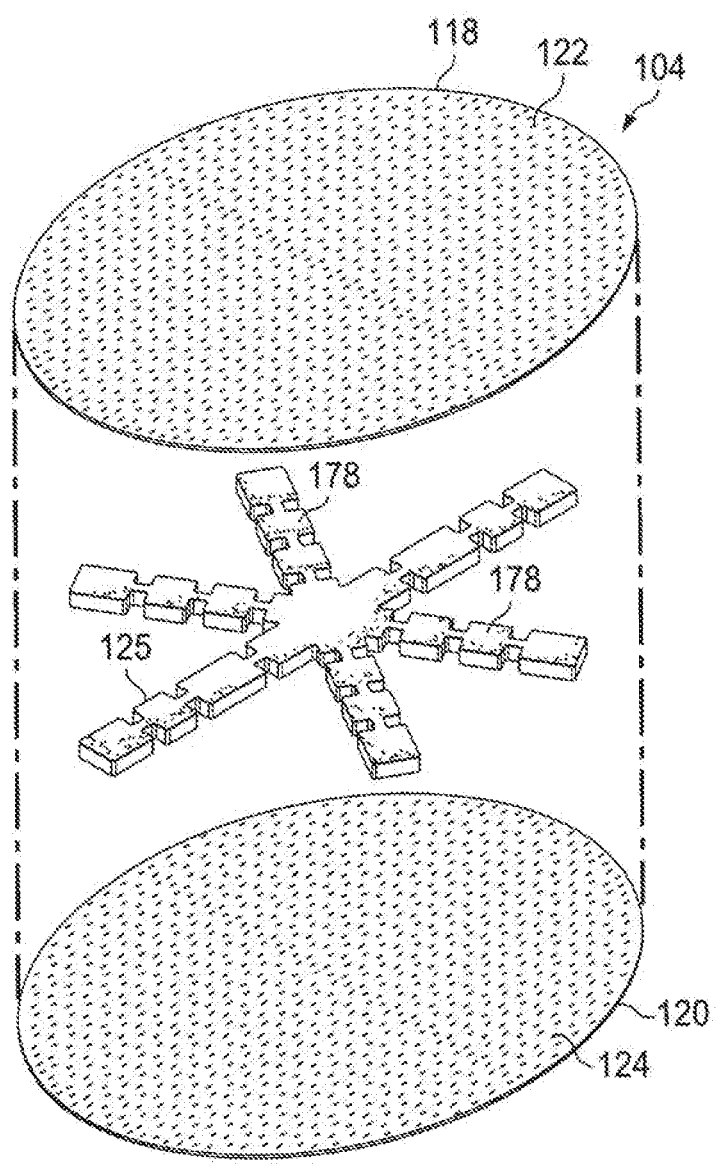
FIG. 7 is a schematic, exploded perspective view of another illustrative abdominal treatment device.
Figure 8:
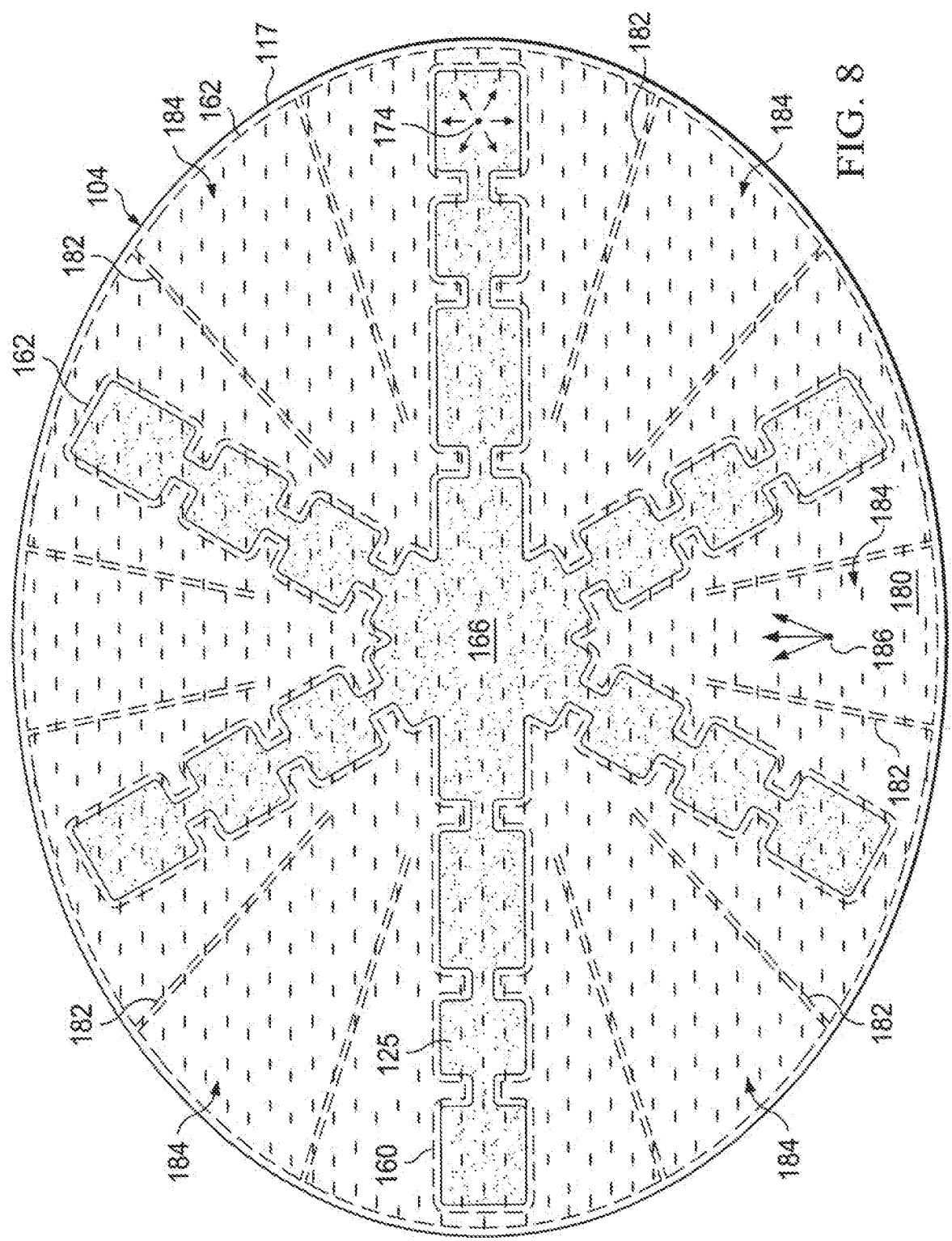
FIG. 8 is a schematic, plan view of the illustrative abdominal treatment device of FIG. 6 shown with an additional feature.

Referring now primarily to FIGS. 7 and 8, another illustrative embodiment of an abdominal treatment device 104 is presented, but in this embodiment, control of the direction of the reduced pressure is desired. The foam spacer 125 is formed as a star with a plurality of spaced leg members 178. Longitudinal bonds 182 have been added to direct fluid flow in a particular direction. Fluids attracted by this embodiment of the abdominal treatment device 104 primarily have flow along the foam spacer 125 and along flow channels 184 formed by the longitudinal bonds 182.

The foam spacer 125 is disposed between the first liquid-impermeable layer 118 and second liquid-impermeable layer 120 of the plurality of liquid-impermeable layers 117. A plurality of bonds 160, including spacer bonds 162, are formed. The spacer bonds 162 around the periphery may be excluded to leave an open intake space between the layers 118, 120 at the periphery. The flow channels 180 are formed by placing the first longitudinal bonds 182 and the second longitudinal bonds 182 at desired locations. The longitudinal bonds 182 and 184 may be formed radially outward from the center portion 166. The longitudinal bonds 182, 184 may begin outboard of the center portion 166 as shown or may go all the way to the center portion 166. Flow channels 180 may be used where increased or directed reduced pressure is more important than guarding against blockage. Analytical control volume 186 shows the reduced pressure vectors may be oriented mainly toward the center portion 166.

In one illustrative approach to using the system 100 for treating the abdominal cavity 102, the abdominal cavity 102 is opened and the abdominal treatment device 104 is deployed within the abdominal cavity 102. The reduced pressure connector subsystem 132 may be fluidly coupled to the abdominal treatment device 104. The reduced pressure connector subsystem 132 may be fluidly coupled to the reduced-pressure source 138 and the reduced-pressure source 138 activated. After use, the abdominal treatment device 104 may be removed through the open abdomen or later through a surgical incision.

The abdominal treatment device 104 may be manufactured, according to one illustrative embodiment, by providing the plurality of liquid-impermeable layers 117 that are fenestrated; stacking the plurality of liquid-impermeable layers 117; and disposing a foam spacer 125 between at least two layers of the plurality of liquid-impermeable layers 117. The plurality of liquid-impermeable layers 117 has a coextensive area $A_1$. The foam spacer 125 disposed between at least two layers of the plurality of liquid-impermeable layers 117 has a plan-view area $A_2$. $A_2$ is less than 80% of $A_1$ (i.e., $A_2 < 0.8 \ A_1$). The foam spacer 125 is configured and positioned such that, under reduced pressure, a target fluid removal zone experiences reduced-pressure vectors over an angle theta ($\theta$) that is greater than 90 degrees.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. An abdominal treatment delivery device for distributing reduced pressure to a tissue site in an abdominal cavity and removing fluids, the abdominal treatment device comprising:
   a plurality of liquid-impermeable layers, wherein the liquid-impermeable layers are at least partially fenestrated;
   a micro-channel space between the liquid-impermeable layers;
   a foam spacer disposed between the liquid-impermeable layers, the foam spacer comprising an elliptical central member, a plurality of arced members concentric with the elliptical central member, each arced member connected to the elliptical central member by a linear member, wherein the liquid-impermeable layers have a coextensive area $A_1$;
   a target fluid removal zone defined by an area bound substantially by an outer peripheral edge of the foam spacer;
   wherein the foam spacer has a plan-view area $A_2$;
   wherein $A_2$ is less than 80% of $A_1$;

wherein the foam spacer is such that, under reduced pressure, a location in the micro-channel space experiences reduced pressure over an angle theta (θ) that is at least 300 degrees.

2. The abdominal treatment device of claim 1, wherein the angle theta (θ) is 360 degrees for more than 70 percent of locations in the micro-channel space.

3. The abdominal treatment device of claim 1, further comprising a stitch bond surrounding the foam spacer and coupling at least two layers of the plurality of liquid-impermeable layers.

4. The abdominal treatment device of claim 1, further comprising a solid bond surrounding the foam spacer and coupling at least two layers of the plurality of liquid-impermeable layers.

5. The abdominal treatment device of claim 1, wherein the target fluid removal zone comprises an area completely enclosed by an outer peripheral edge of the foam spacer.

6. A system for treating an abdominal cavity with reduced pressure, the system comprising:
  an abdominal treatment device for distributing reduced pressure to a tissue site, the abdominal treatment device comprising:
    a plurality of liquid-impermeable layers, wherein the liquid-impermeable layers have a coextensive area $A_1$ and are fenestrated,
    a micro-channel space between the liquid-impermeable layers;
    a foam spacer disposed between the liquid-impermeable layers, the foam spacer having a plan-view area $A_2$, the foam spacer comprising an elliptical central member, a plurality of arced members concentric with the elliptical central member, each arced member connected to the elliptical central member by a linear member;
    a target fluid removal zone defined by an area bound substantially by an outer peripheral edge of the foam spacer;
    wherein $A_2$ is less than 80% of $A_1$,
    wherein the foam spacer is configured such that, under reduced pressure, a location in the micro-channel space experiences reduced pressure vectors over an angle theta (θ) that is at least 300 degrees; and
  a reduced-pressure source fluidly coupled to the abdominal treatment device.

7. The system of claim 6, wherein the angle theta (θ) is 360 degrees for more than 70 percent of locations in the micro-channel space.

8. The system of claim 6, further comprising a reduced-pressure conduit and a reduced-pressure connector subsystem for fluidly coupling the reduced-pressure source to the abdominal treatment device.

9. The system of claim 6, further comprising a stitch bond surrounding the foam spacer and coupling at least two layers of the plurality of liquid-impermeable layers.

10. The system of claim 6, further comprising a solid bond surrounding the foam spacer and coupling at least two layers of the plurality of liquid-impermeable layers.

11. The system of claim 6, wherein the target fluid removal zone comprises an area completely enclosed by an outer peripheral edge of the foam spacer.

* * * * *